United States Patent [19]

Bristol et al.

[11] 4,358,454

[45] Nov. 9, 1982

[54] 1,3,4-TRIAZOLO[1,5-a]PYRIDINES

[75] Inventors: James A. Bristol, Ann Arbor, Mich.; Raymond G. Lovey, West Caldwell, N.J.

[73] Assignee: Schering Corporation, Kenilworth, N.J.

[21] Appl. No.: 338,454

[22] Filed: Jan. 8, 1982

[51] Int. Cl.³ .................... A61K 31/53; C07D 471/04
[52] U.S. Cl. .................................. 424/256; 542/414; 542/426; 542/429; 542/431; 546/119; 424/263
[58] Field of Search ............... 546/119; 542/414, 426, 542/429, 431; 424/256, 263

[56] References Cited

U.S. PATENT DOCUMENTS 4,209,626  6/1980  Trust et al. ...................... 424/256

*Primary Examiner*—Henry R. Jiles
*Assistant Examiner*—Bernard Dentz
*Attorney, Agent, or Firm*—Gerald S. Rosen; Bruce M. Eisen

[57] ABSTRACT

There are disclosed herein certain 1,3,4-triazolo[1,5-a]pyridine compounds which are useful in the treatment of peptic ulcer diseases.

17 Claims, No Drawings

1,3,4-TRIAZOLO[1,5-a]PYRIDINES

SUMMARY OF THE INVENTION

This invention relates to certain 1,3,4-triazolo[1,5-a]pyridine compounds, pharmaceutical compositions thereof, novel processes and intermediates for making said compounds, and methods of treating peptic ulcer disease utilizing said compounds.

More particularly, this invention relates to compounds represented by the structural formula:

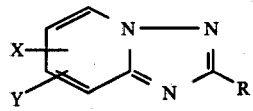

and pharmaceutically acceptable salts thereof, wherein R represents hydrogen, lower alkyl of 1-3 carbons, arylalkyl —CH$_2$OH, —CH$_2$CN,

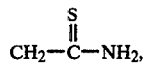

—N(R$_3$)$_2$ (wherein each R$_3$ independently is hydrogen, lower alkyl of 1-3 carbons or arylalkyl), —NO$_2$, —NO, —CH$_2$—O—CO—R$_1$ (wherein R$_1$ is lower alkyl or dimethylaminoethyl), —S(O)$_n$—CH$_3$ or —CH$_2$—S(O)$_n$—CH$_3$ wherein n is zero, one or two; X represents hydrogen, lower alkyl, halogen, hydroxy, lower alkoxy, or trifluoromethyl; and Y represents —R$_2$, —OR$_2$, —NHR$_2$, or —S(O)$_n$R$_2$ wherein n is zero, one or two and wherein R$_2$ is lower alkylene-vinyl, lower alkylene-Ar,-lower alkene-Ar, -lower alkene-lower alkylene-Ar or -lower alkylene-O-Ar, wherein Ar is substituted-phenyl, phenyl, thienyl or pyridyl wherein there are one or more substituents on the substituted phenyl independently selected from —H, —Cl, F, —CH$_3$, —t-butyl, —CF$_3$, —OCH$_3$ and —OH; provided that when R$_2$ is -lower alkylene-O—Ar, Y is not —OR$_2$, —NHR$_2$, or —S(O)$_n$R$_2$.

The preferred compounds of Formula I are those in which Y is in position -8 and R represents —H, —CH$_3$, —CH$_2$OH, —CH$_2$CN, —CH$_2$OCOCH$_3$,

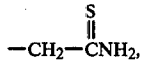

—NH$_2$ or —NO;

X represents hydrogen; and
Y represents —OR$_2$, —NHR$_2$ or —R$_2$ wherein R$_2$ is —CH$_2$—Ar, —CH$_2$—CH$_2$—Ar,

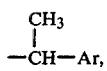

—CH$_2$—CH$_2$—CH$_2$—Ar, —CH=CH—Ar, —CH=CH—CH$_2$—Ar or —CH$_2$—O—Ar, wherein Ar is phenyl, o- or p-fluorophenyl, p-chlorophenyl, 2,4,6-trimethylphenyl, 2-thienyl or 3-thienyl, provided that when R$_2$ is —CH$_2$—O—Ar, Y is not —OR$_2$ or —NHR$_2$.

Thus, the preferred Y substituents of Formula I include phenylmethoxy, phenylmethanamino, thienylmethoxy, thienylmethanamino, phenylethyl, phenylpropyl, thienylethyl, thienylpropyl, 2-phenylethenyl, 3-phenyl-1-propenyl or phenoxymethyl.

The most preferred compounds of this invention are represented by the formula:

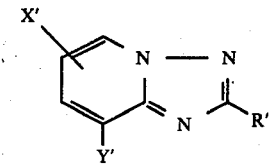

and pharmaceutically acceptable salts thereof, wherein R', is hydrogen, methyl, amino or cyanomethyl;
X' is hydrogen; and
Y' is phenylmethoxy, phenylmethanamino, phenylethyl, 3-phenyl-1-propenyl or 2-phenylethenyl.

As used herein "halogen" means fluorine, chlorine, bromine or iodine with chlorine and fluorine preferred. The term "lower" as it modifies radicals such as alkyl, alkene, alkylene, alkoxy and the like, unless otherwise stated, means straight and branched-chain radicals having up to six carbon atoms, e.g. methyl, ethyl, propyl, butyl, t-butyl, isopropyl, neopentyl, dimethylbutyl 3-propenyl, alkyl, ethenyl, methylene, ethylene, propylene, butylene and the like. Methyl is the preferred lower alkyl.

"Pyridyl" includes the 2-, 3- and 4-isomers and their halogen and lower alkyl substituted analogs; "thienyl" includes the 2- and 3-isomers and their halogen and lower alkyl substituted analogs. The substituents on the "substituted-phenyl" radical may be in the ortho, meta and/or para positions; the preferred substituent is halogen. In those compounds in which X is other than hydrogen, it may be at any of the 5-,6-,7- or 8-positions not already substituted by the Y-substituent. "Pharmaceutically acceptable salts" include salts formed by the reaction of the compounds represented by Formula I with pharmaceutically acceptable acids using conventional means. Such acids can be organic or inorganic, e.g. hydrochloric, sulfuric, phosphoric, nitric, acetic, propionic, maleic, ascorbic, citric, and the like.

Examples of 1,3,4-triazolo[1,5-a]pyridine compounds within the scope of this invention are:
1. 8-Phenylmethoxy-1,3,4-triazolo[1,5-a]pyridine;
2. 8-(2-Fluorophenylmethoxy)-2-methyl-1,3,4-triazolo[1,5-a]pyridine;
3. 8-Phenylmethoxy-1,3,4-triazolo[1,5-a]pyridine-2-acetonitrile;
4. 8-Phenylmethoxy-2-hydroxymethyl-1,3,4-triazolo[1,5-a]pyridine;
5. 8-(2-Phenylethyl)-2-methyl-1,3,4-triazolo[1,5-a]pyridine;
6. 8-(2-Phenylethyl)-1,3,4-triazolo[1,5-a]pyridine-2-acetonitrile;
7. 8-(3-Phenyl-1-propenyl)-2-methyl-1,3,4-triazolo[1,5-a]pyridine;
8. 8-(3-Phenyl-1-propenyl)-2-amino-1,3,4-triazolo[1,5-a]pyridine;
9. 8-(3-Thienylmethoxy)-1,3,4-triazolo[1,5-a]pyridine-2-acetonitrile;
10. 8-(3-Thienylethyl)-1,3,4-triazolo[1,5-a]pyridine-2-acetonitrile;
11. 8-Phenylmethoxy-2-nitroso-1,3,4-triazolo[1,5-a]pyridine;
12. 8-Phenylmethoxy-2-acetoxymethyl-1,3,4-triazolo[1,5-a]pyridine;

13. 8-(2-Phenylethyl)-1,3,4-triazolo[1,5-a]pyridine-2-thioacetamide;
14. 8-Phenylmethanamino-2-methyl-1,3,4-triazolo[1,5-a]pyridine;
15. 8-Phenylmethanamino-1,3,4-triazolo[1,5-a]pyridine-2-acetonitrile.
16. 8-(2-phenylethenyl)-2-methyl-1,3,4-triazolo[1,5-a]pyridine;
17. 8-(2-phenylethenyl)-2-amino-1,3,4-triazolo[1,5-a]pyridine;
18. 8-(2-phenylethenyl)-1,3,4-triazolo[1,5-a]pyridine-2-acetonitrile;
19. 8-[2-(3-thienyl)ethenyl]-2-methyl-1,3,4-triazolo[1,5-a]pyridine;
20. 8-[2-(3-thienyl)ethenyl]-2-amino-1,3,4-triazolo[1,5-a]pyridine; and
21. 8-[2-(3-thienyl)ethenyl]-1,3,4-triazolo[1,5-a]pyridine-3-acetonitrile.

DETAILED DESCRIPTION

The compounds of this invention can be prepared by various and alternative methods, depending on the products desired.

The 1,3,4-triazolo[1,5-a]pyridines substituted in the 2-position as well as 5-,6-,7- and/or 8-positions can be prepared by reacting 2-aminopyridine having the corresponding substituent in the 6-,5-,4- and/or 3-position with a cyano compound substituted with the moiety being introduced to the 2-position, followed by cyclization with a suitable oxidizing agent such as lead tetraacetate as described by Bower et al., J. Chem. Soc., 4506 (1957), as illustrated in the following reaction Scheme 1.

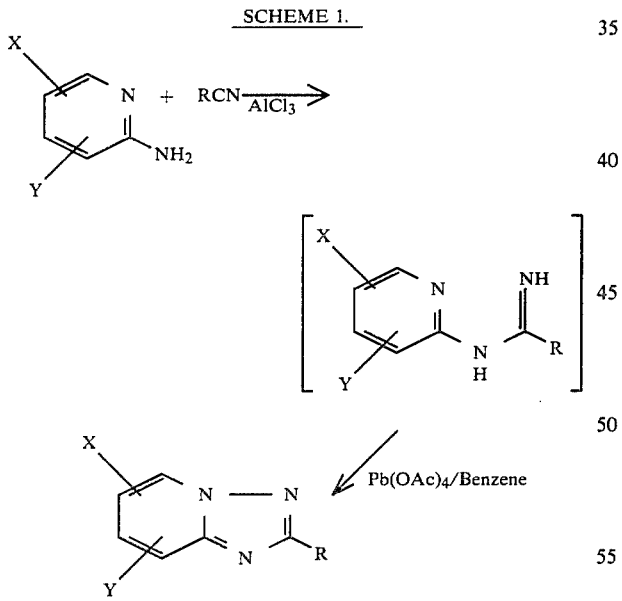

SCHEME 1.

The reaction between the pyridine and the cyano compound is catalyzed by a Lewis Acid catalyst, such as aluminum trichloride, at temperatures from about 20° C. to 200° C. The cyclization occurs in a suitable inert solvent, such as benzene, at temperatures from about 20° C. to 200° C. The 2-amino-3-substituted pyridine starting materials for the most preferred compounds of this invention, the 8-substituted-1,3,4-triazolo[1,5-a]pyridines, as depicted in formula I are either known compounds or can be prepared by known methods, e.g. those disclosed in EPA publication No. 0033094, Aug. 5, 1981 which discloses the preparation of 2-amino-3-phenylmethoxypyridine by reacting 2-amino-3-hydroxypyridine with benzyl chloride in a basic medium. Other 3-arylalkoxypyridines are shown to be prepared in the same manner by reacting 2-amino-3-hydroxypyridine with the appropriate arylalkylhalide.

In addition, appropriate 2-amino-3-arylalkoxypyridines also may be synthesized from 2-amino-3-hydroxypyridine by the procedure described in Acta. Chem. Scand. 23, 1791 (1969).

2-Amino-3-benzylaminopyridine, as shown in EPA publication No. 0033094, can be prepared by reacting 2,3-diaminopyridine with benzyl bromide. Other 2-amino-3-arylaminopyridines can be prepared by reacting 2,3-diaminopyridine with the appropriate arylalkylhalide.

2-Amino-3-(2-phenylethyl)pyridine is prepared by reacting sodium amide and 3-(2-phenylethyl)pyridine at about 160° C.–167° C.

Similarly, the 2-amino substituent can be incorporated into the pyridine on other 3-(arylalkyl)pyridines.

Alternatively, 2-hydrazino-3-,4-,5- or 6-nitropyridine can be reacted with an organic carboxylic acid at temperatures of about 20° C. to 200° C. to produce 2-[R-substituted]-8-, 7-, 6-, or 5-nitro-1,3,4-triazolo[1,5-a]pyridine, respectively, as shown in the following reaction Scheme 2.

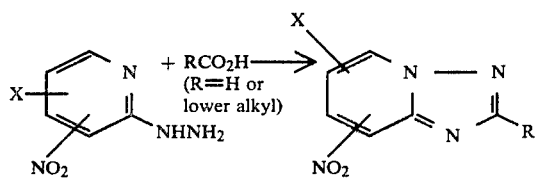

The nitro substituent (8-position preferred) can then be reduced by conventional means to an amino group which can subsequently be N-alkylated as shown in the following reaction Scheme 3.

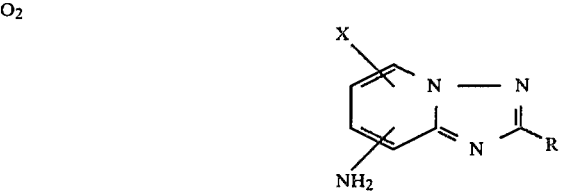

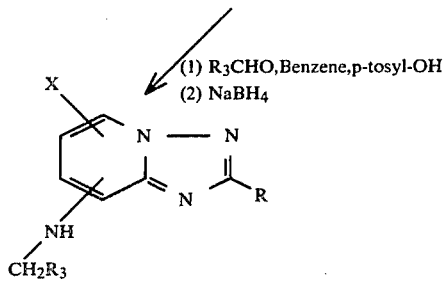

In addition, the amino group can be transformed by conventional diazotization means to hydroxy, halogen or cyano groups. The compounds containing these groups can be used as intermediates for preparing useful 1,3,4-triazolo[1,5-a]pyridine compounds of this invention. The transformations are shown in the following reaction Scheme 4.

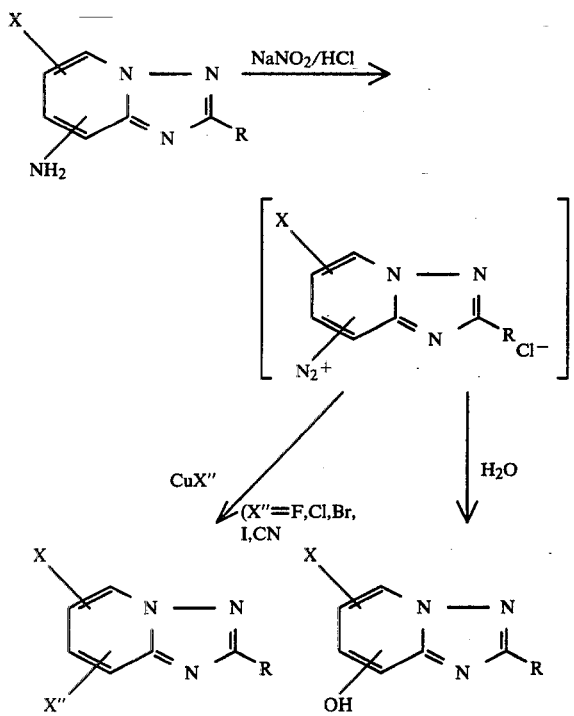

An example of the use of the compounds made by reaction Scheme 4 as an intermediate is the conversion of the cyano group (for illustrative purposes at the 8-position) to a formyl group by e.g. diisobutyl aluminum hydride (DIBAL) reduction, followed by conversion of the formyl group into an olefinic group. The olefinic group can, if desired, be saturated by conventional means, as shown in the following reaction Scheme 5.

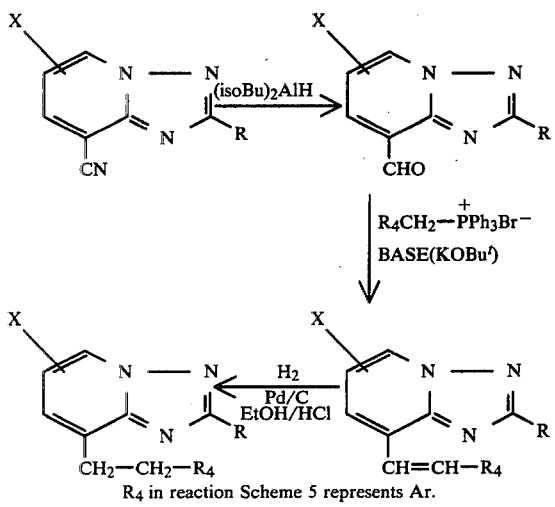

R4 in reaction Scheme 5 represents Ar.

Also useful as intermediates for compounds of this invention are the 2-methyl-1,3,4-triazolo[1,5-a]pyridines substituted in the 5-,6-,7- or 8-positions. The preparations of the 2-methyl compounds are shown in reaction Schemes 1-5 wherein R is methyl. An example of the use of the 2-methyl compound as an intermediate is the preparation of the 2-chloromethyl compound by chlorination using N-chlorosuccinimide in a suitable solvent such as carbon tetrachloride. This latter compound may be converted to various derivatives by nucleophilic substitution in which the chlorine atom is displaced. For example, treatment of the 2-chloromethyl compound with an alkali metal cyanide such as sodium cyanide in a suitable solvent such as dimethyl sulfoxide, ethanol or dimethyl formamide (DMF) yields the 2-cyanomethyl compound. This latter compound can be further converted to the 2-thioacetamide compound by treatment with hydrogen sulfide in pyridine.

The 2-chloromethyl compound can also be converted to the 2-hydroxymethyl compound by treatment with an alkali metal hydroxide such as sodium hydroxide in an aqueous solvent, e.g. acetonitrile-water. The 2-hydroxymethyl compound can be transformed to an ester by treatment with an acid halide or anhydride in inert solvent.

The above reactions are depicted in the following reaction Scheme 6.

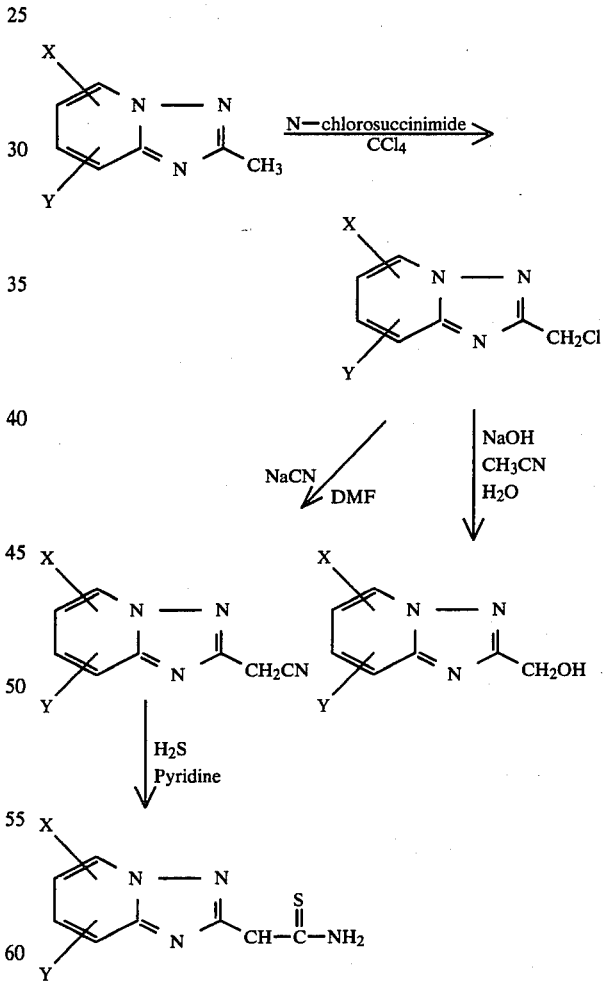

In the case were R is hydrogen, the hydrogen can be replaced by other substituents to make useful compounds of this invention. For example, the 2-nitro compound can be made by reacting the corresponding 2-hydrogen compound with a mixture of nitric and sulfuric acids. Alternatively, the 2-nitroso compound can be made by reacting the 2-hydrogen compound with either sodium nitrite in hydrochloric acid solution or with an alkyl nitrile such as n-butyl nitrite. The nitration reactions are shown in reaction Scheme 7.

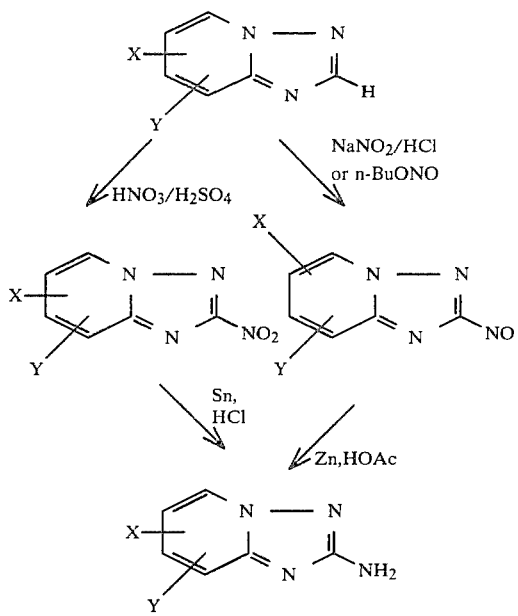

The 1,3,4-triazolo[1,5-a]pyridine compounds of this invention are useful in the treatment of peptic ulcers. They display chemotherapeutic activity which enables them to relieve the symptoms of peptic ulcer disease, including stress ulceration, and promote healig of gastric and/or duodenal ulcers. The anti-ulcer activity of the compounds of this invention is identified by tests which measure their cytoprotective effect (also referred to as mucoprotective effect) and anti-secretory effect in rats. The compounds are also useful as conjunctive therapeutic agents for coadministration with such anti-inflammatory/analgesic agents as aspirin, indomethacin, phenylbutazone, ibuprofen, naproxen, tolmetin and other agents having the untoward side effect of contributing irritation and damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease, duodenal ulcer disease and drug-induced gastric ulceration. Such tests include testing for antisecretory effects in rats using the pyloric ligation technique in which the test compounds are administered in appropriate and well-known vehicles either intraperitoneally or orally.

In cytoprotective tests in rats in which ethanol is employed to induce gastrointestinal damage, the compounds of this invention are found to be effective for the oral treatment of the ulcerative disease states mentioned herein at doses of about 0.5–50 mg/kg of body weight per day. Preferably the total dosages are administered in 2 to 4 divided doses per day.

When administered parenterally, e.g. intravenously, the compounds are administered at dosage range of about 0.01 to 10 mg/kg body weight in single or multiple daily doses. Of course, the dosage administration to a particular patient is variable and will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably about 600–800 mg/day, in two to four divided doses. This dosage regimen achieves relief of the symptoms of peptic ulcer disease and promotes the healing of gastric and/or duodenal ulcers.

To treat peptic ulcer disease, gastric and duodenal ulcers, and prevent and treat drug-induced gastric ulceration, the active compounds of this invention can be administered in unit dosage forms such as tablets, capsules, pills, powders, granules, sterile parenteral solutions or suspensions, suppositories and the like. Such dosage forms are prepared according to standard techniques well known in the art.

The following example illustrates the preparation of compounds of this invention. All temperatures are in degrees Celsius.

EXAMPLE

2-Methyl-8-phenylmethanamino-1,3,4-triazolo[1,5-a]pyridine 3.8 g 8-Amino-2-methyl-1,3,4-triazolo[1,5-a]pyridine prepared as described by Potts, et al., J. Heterocyclic Chem., 7, 1019 (1970), 2.7 g benzaldehyde, 0.042 g para-toluenesulfonic acid and 400 ml benzene were heated together under reflux. The water formed was removed using a Dean-Stark trap. After 18 hrs., the mixture was allowed to cool and the solvent removed in vacuo. The solid residue obtained was dissolved in 200 ml methanol and 1.6 g sodium borohydride was added in portions, with stirring. After 2 hours the methanol was removed in vacuo and the residue partitioned between 200 ml methylene chloride and 200 ml water. The organic layer was separated and dried over anhydrous potassium carbonate. After filtration, the solvent was removed in vacuo. The resulting crystalline product was determined by spectroscopic and elemental analysis to be 2-methyl-8-phenylmethanamino-1,3,4-triazolo[1,5-a]pyridine. It has a melting point of 83°–85° and is crystallized from hexanes.

8-phenylmethanamino-1,3,4-triazolo[1,5-a]pyridine-2-acetonitrile can be prepared according to the process described in reaction Scheme 6 using the compound prepared in the above Example as the starting material.

The following formulations exemplify some of the dosage forms in which the compounds of this invention may be employed. In each, the active ingredient is designated by the term "Drug" which is meant to indicate one of the following compounds:

2-methyl-8-phenylmethanamino-1,3,4-triazolo[1,5-a]pyridine and
8-phenylmethanamino-1,3,4-triazolo[1,5-a]pyridine-2-acetonitrile.

It is contemplated, however, that each of these examplar compounds may be replaced by equally effective quantities of other compounds within the scope of Formula I.

| | Formulation 1 Tablets | | |
|---|---|---|---|
| No. | Ingredient | mg/tab | mg/tab |
| 1 | Drug | 25.0 | 400.0 |

-continued

Formulation 1
Tablets

| No. | Ingredient | mg/tab | mg/tab |
|---|---|---|---|
| 2 | Lactose, impalpable powder USP | 114.0 | 241.5 |
| 3 | Corn starch USP | 25.0 | 50.0 |
| 4 | Corn starch as 5% paste in distilled water | 10.0 | 35.0 |
| 5 | Corn starch USP | 25.0 | 50.0 |
| 6 | Magnesium stearate USP | 1.0 | 3.5 |
|   |   | 200.0 | 780.0 |

METHOD OF MANUFACTURE

Mix items nos. 1, 2 and 3 in a suitable blender for 5 to 15 minutes. Pass through a fine screen (#40) if necessary. Reblend for 5 to 10 minutes and granulate with item no. 4. Pass the damp granulated mass through a coarse sieve (#6) using a suitable mill. Dry the damp granules at 40° to 50° C. overnight. Mill the dried granules using a no. 20 screen. Add item no. 5 and blend for 5 to 10 minutes. Add item no. 6 and blend further for 3 to 5 minutes. Compress the tablet mixture into tablets of an appropriate size and weight using a suitable tableting machine.

Formulation 2
Capsules

| No. | Ingredient | mg/tab | mg/tab |
|---|---|---|---|
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium stearate USP | 1.0 | 3.5 |
|   |   | 200.0 | 700.0 |

METHOD OF MANUFACTURE

Mix items nos. 1, 2 and 3 in a suitable blender for 5 to 10 minutes. Pass through a fine screen (#40) if necessary. Reblend for 5 to 10 minutes, add item no. 4 and mix further for 3 to 50 minutes. Using a suitable machine, encapsulate the mixture into a two piece hard gelatin capsule of appropriate size.

Formulation 3
Suspensions

| Ingredients | Formula A (mg/ml) | Formula B (mg/ml) |
|---|---|---|
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

METHOD OF MANUFACTURE

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. Dilute suspension to final volume with purified water at 25° C.

Formulation 4
Parenteral

|   | mg/ml |
|---|---|
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

METHOD OF MANUFACTURE

1. Dissolve parabens in a portion (approximately 85% of the final volume) of the water for injection at 65°–70° C.
2. Cool to 25°–35° C. Charge and dissolve sodium bisulfite, disodium edetate and sodium sulfate.
3. Charge and dissolve the Drug.
4. Bring the solution to the final volume by adding water for injection.
5. Filter the solution through 0.22 micron membrane and fill into appropriate containers.
6. Terminally sterilize the units by autoclaving.

Formulation 5
Injectable Suspension

|   | mg/ml |
|---|---|
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

METHOD OF PREPARATION

1. Dissolve parabens in a portion of water for injection at 65°–70° C.
2. Cool to 25°–35° C. Charge and dissolve benzyl alcohol, sodium citrate, disodium edetate, PEG 4000, povidone and sodium carboxymethylcellulose.
3. Filter the solution and sterilize by autoclaving
4. Make a slurry of the sterile Drug and pass it through a colloid mill.
5. Mix it well with solution from Step 3 and pass it through the mill.
6. Bring the suspension to the final volume/weight and fill into sterile containers.

Formulation 6
Suppositories

| A. | Formula | mg/supp |
|---|---|---|
|   | Drug | 5.0 |
|   | Cocoa butter | 1995.0 |
|   |   | 2000.0 mg (2.0 g.) |

PROCEDURE

1. Melt cocoa butter to about 32°–35° C.
2. Blend Drug into cocoa butter until well dispersed.
3. Pour into teflon-coated mold and congeal in refrigerator. Keep in refrigerator for an appropriate length of time.
4. Remove suppositories from mold.

| B. | Formula | mg/supp |
|---|---|---|
|  | Drug | 100.0 |
|  | PEG 1000 | 1824.0 |
|  | PEG 4000 | 76.0 |
|  |  | 2000.0 mg (2.0 g.) |

PROCEDURE

1. Melt PEG 1000 and PEG 4000 in one container to 50° C.
2. Add Drug to the mixture. Blend until well dispersed.
3. Pour into mold and congeal in refrigerator. Keep in refrigerator for an appropriate length of time.
4. Remove suppositories from mold.

We claim:

1. A compound represented by the formula:

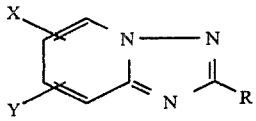

and the pharmaceutically acceptable salts thereof, wherein R represents hydrogen, lower alkyl of 1–3 carbons, arylalkyl, —CH$_2$OH, —CH$_2$CN,

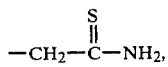

—NO$_2$, —NO, —CH$_2$—O—CO—R$_1$, (wherein R$_1$ is lower alkyl or dimethylaminomethyl), —N(R$_3$)$_2$ (wherein each R$_3$ independently is hydrogen, lower alkyl of 1–3 carbon atoms or arylalkyl), —S(O)$_n$—CH$_3$ or —CH$_2$—S(O)$_n$—CH$_3$ wherein n is zero, one or two; X represents hydrogen, lower alkyl, halogen, hydroxy, lower alkoxy, or trifluoromethyl; and Y represents —R$_2$, —OR$_2$, —NHR$_2$, or —S(O)$_n$R$_2$ wherein n is zero, one or two and R$_2$ is -lower alkylene-vinyl, -lower alkylene-Ar, -lower alkene-Ar, -lower alkene-lower alkylene-Ar, or -lower alkylene-O-Ar, wherein Ar is substituted-phenyl, phenyl, thienyl, or pyridyl wherein there are one or more substituents on the substituted-phenyl independently selected from —H, —Cl, —F, —CH$_3$, -t-butyl, —CF$_3$, —OCH$_3$ and —OH; provided that when —R$_2$ is lower alkylene-O—Ar, Y is not —OR$_2$, —NHR$_2$ or —S(O)$_n$R$_2$.

2. A compound of claim 1 wherein
R represents —H, —CH$_3$, —CH$_2$OH, —CH$_2$CN, —CH$_2$OCOCH$_3$,

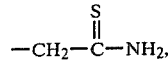

—NH$_2$ or —NO;
X represents hydrogen; and
Y is in the 8-position and represents —OR$_2$, —NHR$_2$ or —R$_2$ wherein R$_2$ is —CH$_2$—Ar, —CH$_2$—CH$_2$—Ar,

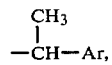

—CH$_2$—CH$_2$—CH$_2$—Ar, —CH=CH—Ar, —CH=CH—CH$_2$—Ar or —CH$_2$—O—Ar, wherein Ar is phenyl, o- or p-fluorophenyl, p-chlorophenyl, 2,4,6 trimethylphenyl, 2-thienyl or 3-thienyl, provided that when R$_2$ is —CH$_2$—O—Ar, Y is not —OR$_2$ or —NHR$_2$.

3. A compound of claim 1 wherein Y is phenylmethoxy, phenylmethanamino, thienylmethanamino, phenylethyl, phenylpropyl, thienylethyl, thienylpropyl, 2-phenylethenyl, 3-phenyl-1-propenyl or phenoxymethyl.

4. A compound of claim 1 represented by the formula:

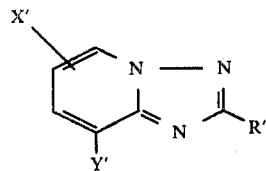

and pharmaceutically acceptable salts thereof, wherein
R' represents hydrogen, methyl, amino or cyanomethyl;
X' represents hydrogen; and
Y' represents phenylmethoxy, phenylmethanamino, phenylethyl, 3-phenyl-1-propenyl or 2-phenylethenyl.

5. The compound of claim 4 wherein
R' is methyl and Y' is phenylmethanamino, i.e. 2-methyl-8-phenylmethanamino-1,3,4-triazolo[1,5-a]pyridine.

6. The compound of claim 4 wherein R' is cyanomethyl, and Y' is phenylmethanamino, i.e. 8-phenylmethanamino-1,3,4-triazolo[1,5-a]pyridine-2-acetonitrile.

7. A method for the treatment of the symptoms of peptic ulcer disease in mammals, which comprises administering to a mammal having peptic ulcer disease a therapeutically effective amount of a compound of claim 1.

8. A method for the treatment of gastric ulcers in mammals which comprises administering to a mammal having gastric ulcers a therapeutically effective amount of a compound of claim 1.

9. A method for the treatment of duodenal ulcers in mammals which comprises administering to a mammal having duodenal ulcers a therapeutically effective amount of a compound of claim 1.

10. A method for inhibiting the formation of gastrointestinal irritation and damage and ulcers due to administration of drugs which induce such effects which comprises administering to a patient in need of such treatment a therapeutically effective amount of a compound of claim 1 during the term said gastrointestinal irritating and damaging drug is being administered for its therapeutic effect.

11. A method for the treatment of gastrointestinal damage due to stress which comprises administering to a mammal suffering from such damage a therapeutically effective amount of a compound of claim 1.

12. A method of claim 7 which comprises administering to a mammal having peptic ulcer disease, a therapeutically effective amount of a compound of claim 5.

13. A method of claim 7 which comprises administering to a mammal having peptic ulcer disease, a therapeutically effective amount of a compound of claim 6.

14. A pharmaceutical formulation for use in the treatment of ulcers which comprises a compound of claim 1 in a therapeutically effective amount sufficient to alleviate the symptoms of peptic ulcer disease together with a pharmaceutically acceptable carrier.

15. A pharmaceutical formulation of claim 14 which comprises a therapeutically effective amount of a compound of claim 5 together with a pharmaceutically acceptable carrier.

16. A pharmaceutical formulation of claim 14 which comprises a therapeutically effective amount of a compound of claim 6 together with a pharmaceutically acceptable carrier.

17. A composition of claim 14, 15 or 16 suitable for oral administration.

* * * * *